United States Patent
Hiernard et al.

[11] Patent Number: 5,938,701
[45] Date of Patent: Aug. 17, 1999

[54] EXTRACTION DEVICE

[76] Inventors: Bruno Hiernard, 8 Wiltshire Gardens, Bransgore, Christchurch, Dorset BH23 8BJ; Richard Farrar, Sunnybank House, Lower Pennington Road, Lymington, Hampshire, S041 8AN, both of United Kingdom

[21] Appl. No.: 08/948,467

[22] Filed: Oct. 10, 1997

[30] Foreign Application Priority Data

Nov. 15, 1996 [GB] United Kingdom .................... 9623942

[51] Int. Cl.⁶ ............................................ A61F 2/34
[52] U.S. Cl. ................... 623/22; 606/99; 623/23
[58] Field of Search ............................ 623/22, 18; 606/99

[56] References Cited

U.S. PATENT DOCUMENTS

| | | | |
|---|---|---|---|
| 4,993,410 | 2/1991 | Kimsey | 606/100 |
| 5,098,437 | 3/1992 | Kashuba | 606/89 |
| 5,112,338 | 5/1992 | Anspach, III | 606/99 |
| 5,116,339 | 5/1992 | Glock | 606/91 |
| 5,156,606 | 10/1992 | Chin | 606/86 |

*Primary Examiner*—David H. Willse
*Assistant Examiner*—Suzette J. Jackson

[57] ABSTRACT

An extraction device (10,110) for removing a socket bearing insert (12) from an acetabular cup (14) in an acetabular prosthesis in which an extracting member (30, 130) is adapted for attachment to a groove (20) in the insert (12). The extraction device (10, 110) includes a support in the form of a sleeve (38, 138) which bears against the rim of the acetabular cup (14). The extraction device (10, 110) has means for providing an axial force exclusively between the extracting member (30, 130) and the support such that no force is transmitted to a bone to which the acetabular cup (14) is attached.

10 Claims, 5 Drawing Sheets

EXTRACTION DEVICE

This invention relates to an extraction device for removing an insert from the cup of an acetabular prosthesis.

Acetabular prostheses with inserts of metal socket bearings which receive the femoral ball are known in the art. A known type of prosthesis is the constraint type wherein the bearing encompasses more than half of the ball. The bearing generally consists of two pieces which are placed around the ball and secured to the cup by riveting or screw threads, hence it is difficult to assemble the prosthesis in situ. Instead of assembling the prosthesis in situ, the surgeon was provided with an assembled joint comprising both the femoral and acetabular components.

A variation on the above construction is a metal bearing which encompasses 180° or less of a femoral ball. Attachment between the bearing and the cup is again by means of a screw-thread. With this type of construction, although in situ assembly was not impossible, it was still generally impractical because of the screw thread.

International patent application No. WO93/16662 discloses an improved acetabular prosthesis having a metal socket bearing. The prosthesis disclosed in this document comprises an orientable metal socket bearing the external surface of which has a male taper and a metal cup for fixation to the bone which includes a cavity for receiving the metal socket bearing. The surface of the cavity has a female taper for locking engagement with the male taper of the socket bearing.

The metal socket bearing and the metal cup are generally not greater than a full hemisphere. The taper fit is provided with opposing surfaces which allow a friction lock between the metal socket and the metal cup. The angle of the taper is of key importance to achieve a locking fit between the metal socket bearing and the metal cup.

Due to the locking fit of the taper, it is often difficult to remove the metal socket bearing from the metal cup without disturbing the bone to which the metal cup is fixed.

According to the present invention there is provided an extraction device for removing an insert from an acetabular cup comprising:

an extracting member with attachment means for attachment, in use, to the insert to be removed;

a support adapted for bearing, in use, against the cup portion; and means for providing an axial force exclusively between the extracting member and the support such that no force is transmitted to any bone to which the cup portion is attached.

The means for providing an axial force may be in the form of a screw means acting between the extracting member and the support, the screw means converting a turning force into the axial force. Alternatively, the means for providing an axial force is in the form of a lever arrangement acting between the extracting member and the support.

The support may be in the form of an outer sleeve one end of which bears against the cup portion during the extraction operation.

The attachment means of the extracting member may be in the form of a lip for attachment to the insert such that the axial force is transmitted to the insert.

A central column may be provided to which the axial force is applied, the central column being attached to the extracting member in order to transmit the axial force.

The attachment means of the extracting member may be extendable from the support in order to allow the location of the attachment means onto the insert.

The extracting member may be in the form of at least one member which is moveable to allow the location of the attachment means on the insert.

The extracting member may be in the form of an arc of a cylinder, the arc being no greater than 180 degrees such that the extracting member can be slidably located on the insert. Alternatively, the extracting member may be in the form of a plurality of arms which are either moveable outwardly from the insert or rotatable about a pivot point such that the attachment means can be located or removed from the insert.

The extracting member or members may be biased such that the member disengages the insert when the sleeve is not located over the extracting member.

A locking means may be provided for preventing, in use, the relative rotation of the central column and the support to ensure that all the turning force of the screw means is converted to the axial force.

Embodiments of the present invention are now described with reference to the accompanying drawings, in which.

Figure 1:
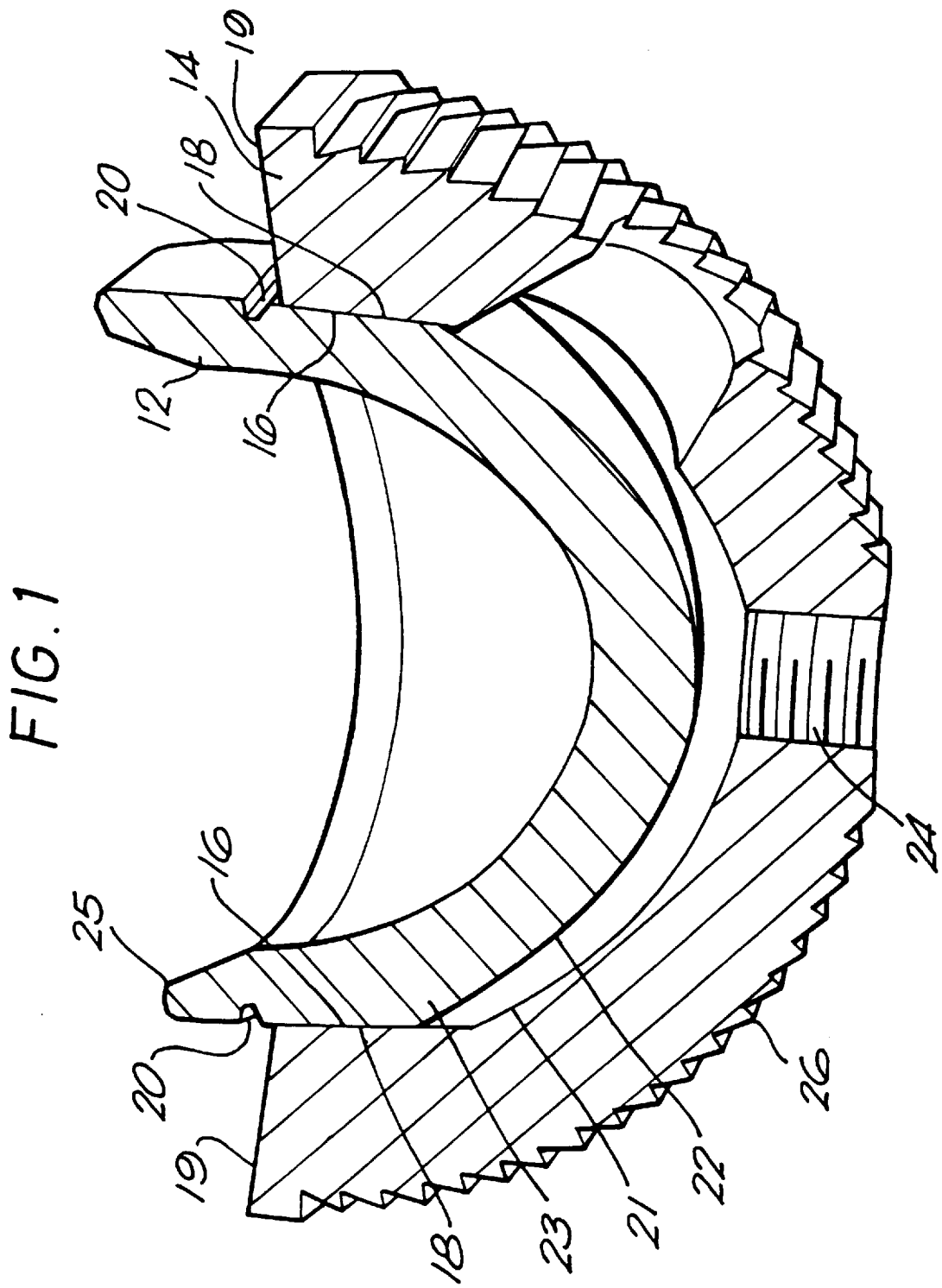
FIG. 1 is a stylised cross-sectional view of an insert and acetabular cup with a taper fit to which an extraction device in accordance with the present invention is applicable.

Referring to the drawings, an acetabular prosthesis has a cup 14 formed of a biocompatible material such as titanium alloy or cobalt chrome the external surface 26 of which is adapted either for cemented or cementless fixation to a bone or prepared acetabular. In the embodiments shown, the external surface 26 is porous coated and stepped for cementless fixation. The cup 14 is attached to a patient's bone. The cup 14 is just less than a full hemisphere and has a rim 19 with a flat surface. An insert 12 in the form of a socket bearing is placed within the cup 14.

The insert 12 and the cup 14 have corresponding tapers 16, 18 which provide a friction lock between the insert 12 and the cup 14. The angle of the tapers 16, 18 is of prime importance to maintain the lock between the insert 12 and the cup 14. The internal surface of the cup 14 adjacent the rim 19 of the cup 14 provides the female taper 18. The tapers 16, 18 are approximately 3–10° half angle, in this embodiment a 5° half angle is use. The surface of the one of the tapers 16, 18 is roughened during turning to achieve better conformity between the male 16 and the female 18 tapers.

The internal surface 21 of the cup 14 continues from the female taper 18 into a rounded bottom of the cup 14 before leading into a threaded apical instrumentation or viewing hole 24.

The insert 12 is formed of a suitable material such as cobalt chromium alloy or a ceramic material the outside surface 23 of which includes the male taper 16 which matches the female taper 18 in angle. A controlled clearance of nominally one millimeter is provided between the bottom 22 of the insert 12 and the internal surface 21 of the cup 14.

Importantly, the insert 12 has a circumferential groove 20 continuous or discontinuous in the outer surface 23 of the insert 12. The groove 20 is disposed below the rim 25 of the insert 12 and above the portion of the male taper 16 which locks with the female taper 18 of the cup 14. The groove 20 remains exposed above the rim 19 of the cup 14.

Figure 2:
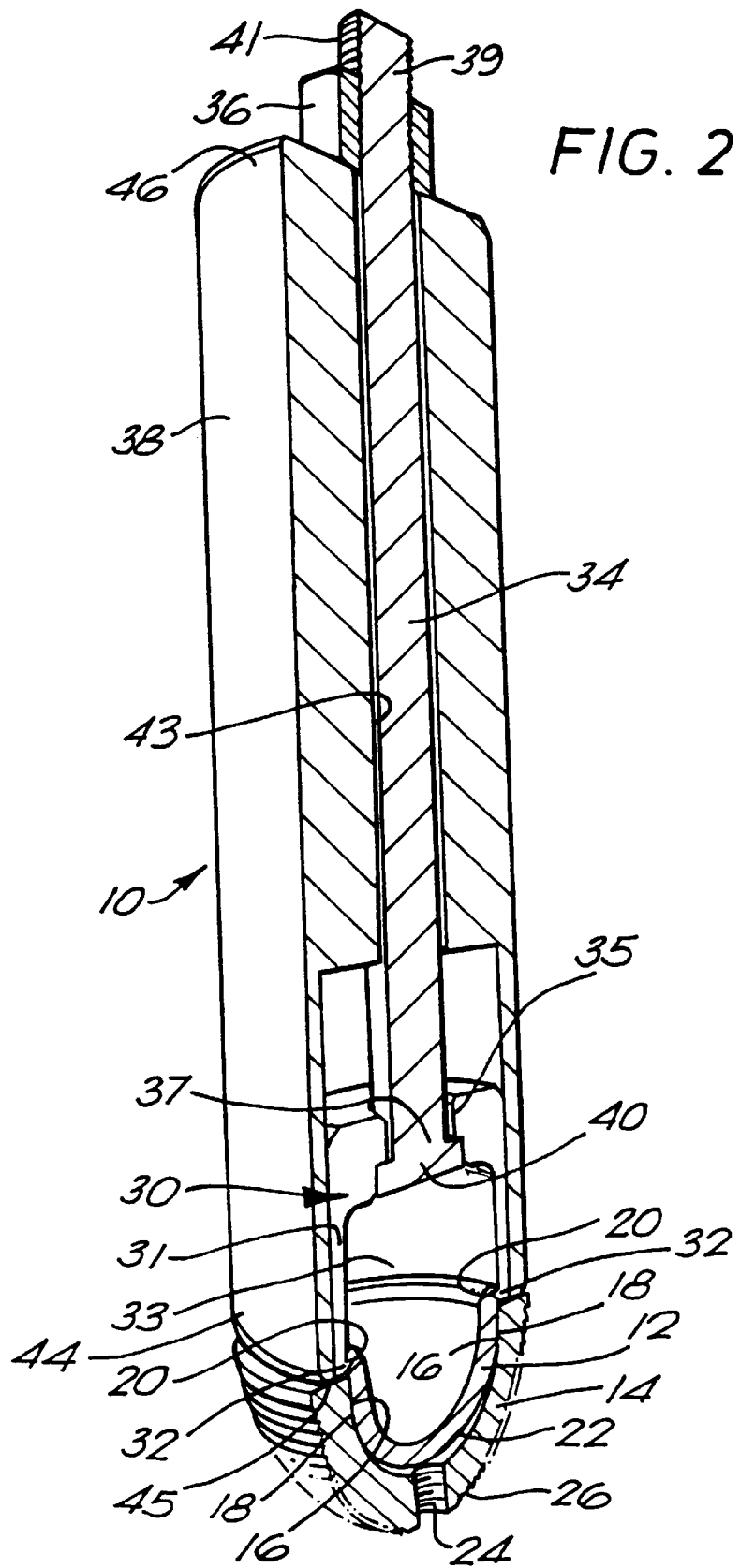
FIG. 2 is a stylised perspective cross-sectional view of a first embodiment of an extraction device in accordance with the present invention attached to an insert and an acetabular cup.
Figure 3:
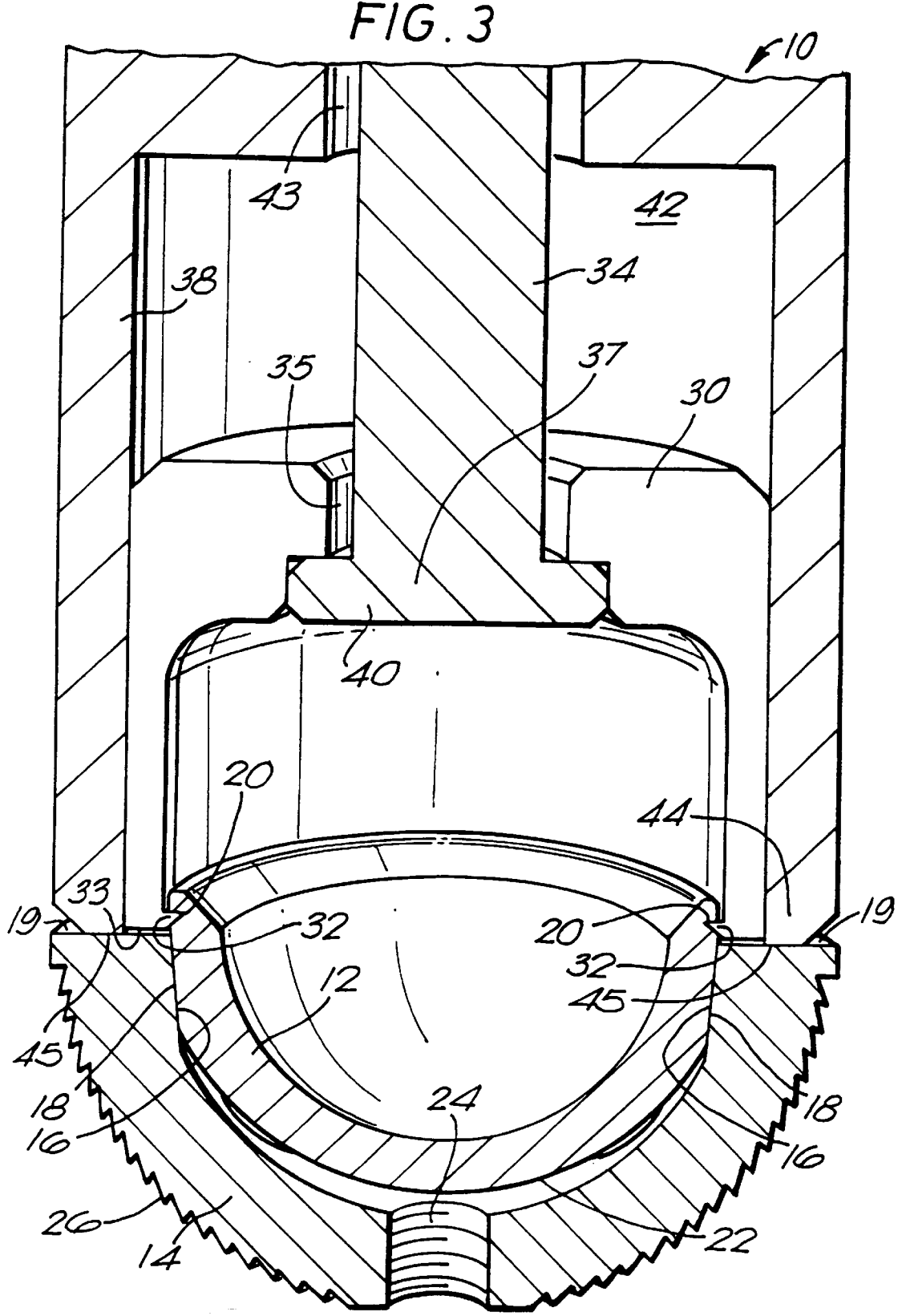
FIG. 3 is a cross-sectional view of a detail of the extraction device of FIG. 2.

Referring to FIGS. 2 and 3, a first embodiment of an extraction device 10 in accordance with the present invention is now described.

The extraction device 10 has an extracting member 30 in the form of a half cylinder component 31 with one closed end. The extracting member 30 has an internally facing lip 32 on the circumferential edge 33 of the open end of the half cylinder 31. The lip 32 is locatable within the groove 20 of the insert 12. The extracting member 30 is formed as a half cylinder 30 to allow the lip 32 to be engaged in the groove 20 by sliding the half cylinder 31 over the rim 25 of the insert 12.

The opposite end of the half cylinder 31 to the open edge 33 is substantially closed with a recess 35 provided in the closed end at the centre of diameter of the half cylinder 31. A central column 34 is provided which extends axially in relation to the half cylinder 31. The central column 34 has a first end 37 in the form of a T-shaped end 40. The central column 34 is located through the central hole 35 in the half cylinder 31 such that the T-shaped end 40 extends within the half cylinder 31 preventing the central column 34 from being fully removed from the half cylinder 31.

A second end 39 of the central column 34 has an external screw thread 41 about which a nut 36 is rotatable.

The extraction device 10 also has a sleeve 38 which surrounds most of the central column 34 with the exception of the second end 39 of the central column 34 about which the nut 36 is located. The sleeve 38 surrounds the extracting member 30 in the form of the half cylinder 31. The sleeve 38 has an inner cavity 42 in which the extracting member 30 is located. The cavity 42 has additional space above the extracting member 30 to allow the extracting member 30 to move slidably within the sleeve 38. The sleeve 38 also has a central bore 43 in which the central column 34 is located.

The sleeve 38 has a first end 44 which is open and which has a flat end surface 45. The flat end 45 acts against the flat rim 19 of the cup 14. The sleeve 38 can be made of more than one piece, the pieces being joined rigidly together by a suitable means. In this way, a gripping surface can be provided on the outer surface of the sleeve 38.

The sleeve 38 has a second end 46 which has an opening in the form of the bore 43 from which the central column 34 extends. The nut 36 acts against the second end 46 of the sleeve 38 as it is rotated about the central column 34.

An anti-rotation device is provided between the central column 34 and the sleeve 38. The anti-rotation device can be in the form of a pin and corresponding slot on the two portions. The slot being linear to allow the axial movement of the central column 34 and the sleeve 38 whilst preventing relative rotation. In this way the sleeve 38 and the central column 34 are rotationally one part.

In use, the extraction device 10 is used to extract an insert 12 from a taper fit with a cup 14 of an acetabular prosthesis, the cup 14 being attached to the patient's bone.

The nut 36 on the central column 34 is loosened to allow the sleeve 38 to be moved along the central column 34 to expose the open edge 33 of the half cylinder 31 of the extracting member 30 which carries the lip 32. The sleeve 38 must also clear the rim 25 of the insert 12. The exposed lip 32 can be slid into half of the circumferential groove 20 of the insert 12. Once the lip 32 has been located in the groove 20, the sleeve 38 can be slid down to cover the extracting member 30. The flat end 45 of the sleeve 38 rests against the flat rim 19 of the cup 14.

The nut 36 is then rotated around the thread 41 of the central column 34 to move the nut 36 towards the T-shaped end 40 of the central column 34. As the nut 36 is rotated about the central column 34, the nut 36 acts against the second end 46 of the sleeve 38.

In order to effect the extraction of the insert 12 from the cup 14, the nut 36 is rotated further about the central column 34. As the nut 36 is rotated, an axial force is developed between the central column 34 and the sleeve 38. The axial movement of the central column 34 is transmitted via the T-shaped end 40 of the central column 34 to the extracting member 30. The extracting member 30 pulls the insert 12 away from the cup 14 whilst the sleeve 38 pushes the cup 14 away from the insert 12 in the opposite direction. The opposing forces are developed exclusively between the insert 12 and the cup 14 ensuring that no force affects the bone to which the cup 14 is fixed.

Once extracted, the insert 12 can be removed from the extraction device 10 by loosening the nut 36 such that the sleeve 38 can again be moved to uncover the lip 32 of the extracting member 30. The insert 12 can then be slidably removed from the extracting member 30.

For the ease of operation of the extraction device 10, the surface of the sleeve 38 can be provided with a gripping surface as this is held in one hand by the operator of the extraction device 10. The other hand of the operator of the extraction device 10 rotates the nut 36. The nut 36 can be provided with a handle for ease of operation.

A second half cylinder can be provided which mirrors the half cylinder 31 resulting in the complete circumference of the groove 20 of the insert 12 being attached to the extraction device 10. In the case of a discontinuous or partial groove 20, the extraction members 31 can each be arcs of less than 180 degrees. In the illustrated half cylinder arrangement, the sleeve 38 needs to be removed sufficiently to uncover the half cylinders to enable the a half cylinders to be located on the groove.

The extracting member 30 can be magnetised to prevent rotation of the extracting member 30 in the sleeve 38. Unwanted rotation can result in positioning problems.

Figure 4:
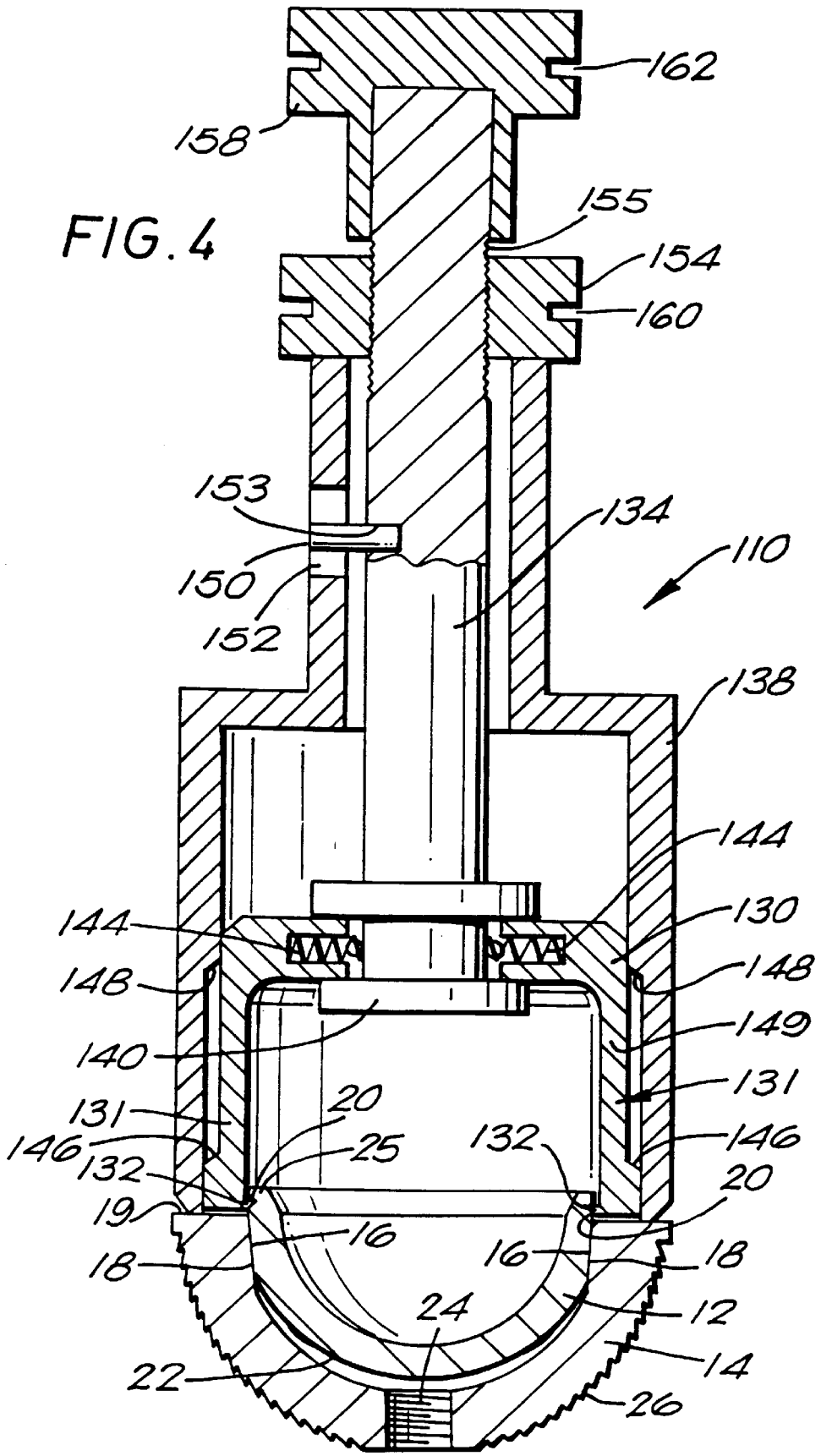
FIG. 4 is a cross-section of a second embodiment of an extraction device in accordance with the present invention attached to an insert and an acetabular cup.

Referring to FIG. 4, a second embodiment of an extraction device 110 is now described. The second embodiment of the extraction device 110 works on the same principle as the first embodiment described above. An axial force is developed between a sleeve 138 and an extracting member 130. The sleeve 138 acts against the flat rim 19 of the cup 14 as in the first embodiment. The extracting member 130 has a lip which locates in the groove 20 of the insert 12 as in the first embodiment.

In this embodiment, the extracting member 130 is in the form of a plurality of arms 131 each having a sprung attachment 144 to a central column 134. The spring attachments 144 are biased such that the arms 131 spring outwardly disengaging the lips 132 from the groove 20 in the insert.

The arms 131 can be circumferentially spaced around the entire rim 25 of the insert 12. The sleeve 138 is movable relative to the extracting member 130 such that the lips 132 and the rim 25 of the insert 12 can be exposed. The arms 131 have a tapered ramp extending outwardly towards the lip carrying end of the arms 131. This ramp 146 acts against the inside surface of the sleeve 138 such that when the sleeve 138 covers the arms 131, the lip 132 on each arm 131 is moved by the sleeve 138 into the groove 20 in the insert 12. The inner surface of the sleeve 138 has a corresponding tapered ramp 148 which acts against the upper portion 149 of each arm 131. Therefore, the upper sleeve 138 must be moved a sufficient distance to clear the taper ramp on the arms 131 to allow the arms biased 131 to spring outwardly disengaging the lip 132 within the groove 20 in the insert 12.

The quick engagement and release of the extracting member(s) 31, 131 from the groove 20 in the insert 12 is important. The lips 32, 132 of the extracting member(s) 31, 131 must move laterally away from the groove 20. This movement can be by sliding as in the first embodiment with the half cylinder or by sprung sideways movement as in the second embodiment with a plurality of arms or by rotation of the arms about a pivot point.

The central column 134 has a T-shaped end 140 as in the first embodiment which locates the central column 134 within the extracting member 130.

A slot 152 is provided in a portion of the sleeve 138 adjacent the central column 134 and a pin 150 is provided for location within the slot 152 and within an aperture 153 in the central column 134. The pin 150 is provided to prevent the central column 134 from rotating when torsion is applied to provide the axial force between the extracting member 130 and the sleeve 138. Alternatively, the pin 150 can be mounted on the sleeve 138 and a slot provided in the central column 134.

In this second embodiment, a nut 154 is provided which corresponds to the nut 36 of the first embodiment. The nut 154 is provided about a threaded portion 155 of the central column 134 directly above the sleeve 138. Rotation of the nut 154 about the central column 134 acts to provide a pulling force on the central column 134 and hence the extracting member 130 whilst pushing down on the sleeve 138 in the same manner as the nut 36 of the first embodiment.

In the second embodiment, the central column 134 extends beyond the nut 154 and a handle 158 is fixedly secured to the central column 134. The operator of the extraction device 110 can grip the nut 154 in one hand. The operator's second hand can grip either the handle 158 or the sleeve 138 to prevent rotation of the central column 134 holds the extraction device 110 stable whilst providing a resistance against the turning force applied to the nut 154.

The nut 154 and the handle 158 can have a number of holes 160, 162 around their circumferences in order to allow a rod to be selectively inserted in the holes 160, 162 to facilitate the turning of the nut 154 and the handle 158. The handle 158 can have a hole through its entire diameter into which a tommy bar can be placed to provide a further grip on the handle 158.

Figure 5:
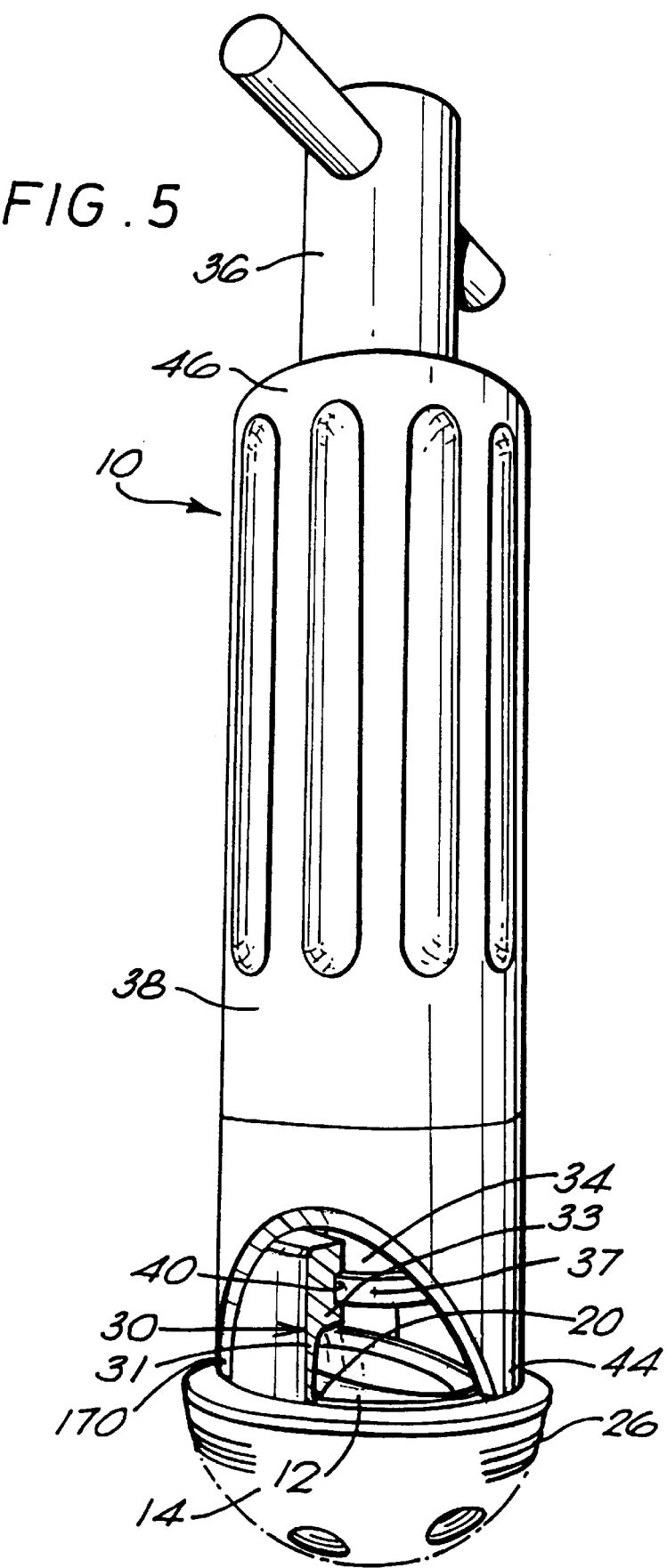
FIG. 5 is a perspective view of a third embodiment of an extraction device in accordance with the present invention attached to an insert and an acetabular cup.

Referring to FIG. 5, a third embodiment of an extraction device 10 is now described. This embodiment is similar to the first embodiment with the additional feature of a curved cut away portion 170 in the sleeve 38 at the first end 44 of the sleeve 38. The cut away portion 170 can be of any shape and is shown in this embodiment to be of elliptical shape and cut into the wall from the first end 44 of the sleeve 38. The cut away portion 170 enables the surgeon to see where to place the extraction device 10 in the groove 20 of the insert 12 and allows better access over bony overhangs. The cut away portion 170 is provided such that the open edge 33 of the half cylinder 31 can be seen. More than one cut-away portion 170 can be provided in the sleeve 38.

The above embodiments describe a screw arrangement for providing the axial force. The axial force between the extracting member and the support could equally be provided by vertical cogs interacting with a grooved central column such as in a lever cork-screw.

Improvements and modifications may be made to the above without departing from the scope of the present invention.

We claim:

1. An extraction device for removing an insert from an acetabular cup comprising:
    an extracting member with attachment means for attachment, in use, to the insert to be removed;
    a support adapted for bearing, in use, against the cup portion; and
    means for providing an axial force exclusively between the extracting member and the support such that no force is transmitted to any bone to which the cup portion is attached;
    wherein the support is in the form of an outer sleeve one end of which bears against the cup portion during the extraction operation;
    wherein a cut away portion extends through the outer sleeve to allow access within the outer sleeve and to enable visual inspection by the surgeon.

2. An extraction device for removing an insert from an acetabular cup comprising:
    an extracting member with attachment means for attachment, in use, to the insert to be removed;
    a support adapted for bearing, in use, against the cup portion; and
    means for providing an axial force exclusively between the extracting member and the support such that no force is transmitted to any bone to which the cup portion is attached;
    wherein the extracting device is magnetized.

3. An extraction device for removing an insert from an acetabular cup comprising:
    an extracting member with attachment means for attachment, in use, to the insert to be removed;
    a support adapted for bearing, in use, against the cup portion; and
    means for providing an axial force exclusively between the extracting member and the support such that no force is transmitted to any bone to which the cup portion is attached;
    wherein the attachment means of the extracting member is in the form of a lip for attachment means to the insert such that the axial force is transmitted to the insert.

4. An extraction device as claimed in claim 3, wherein a central column is provided to which the axial force is applied, the central column being attached to the extracting member in order to transmit the axial force.

5. An extraction device as claimed in claim 3, wherein the attachment means of the extracting member may be extendable from the support in order to allow the location of the attachment means onto the insert.

6. An extraction device for removing an insert from an acetabular cup comprising:
    an extracting member with attachment means for attachment, in use, to the insert to be removed;
    a support adapted for bearing, in use, against the cup portion; and
    means for providing an axial force exclusively between the extracting member and the support such that no force is transmitted to any bone to which the cup portion is attached;
    wherein the attachment means of the extracting member is in the form of at least one extracting member which is moveable to allow the location of the attachment means on the insert; and
    wherein said at least one extracting member is biased such that at least one extracting member disengages the insert when the sleeve is not located over the extracting member.

7. An extraction device for removing an insert from an acetabular cup comprising:
- an extracting member with attachment means for attachment, in use, to the insert to be removed;
- a support adapted for bearing, in use, against the cup portion; and
- means for providing an axial force exclusively between the extracting member and the support such that no force is transmitted to any bone to which the cup portion is attached;
- wherein the extracting member is in the form of an arc of a cylinder, the arc no greater than 180 degrees such that the extracting member can be slidably located on the insert.

8. An extraction device for removing an insert from an acetabular cup comprising:
- an extracting member with attachment means for attachment, in use, to the insert to be removed;
- a support adapted for bearing, in use, against the cup portion; and
- means for providing an axial force exclusively between the extracting member and the support such that no force is transmitted to any bone to which the cup portion is attached;
- wherein the extracting member is in the form of a plurality of arms which are either moveable outwardly from the insert or rotatable about a pivot point such that the attachment means can be located or removed from the insert.

9. An extraction device as claimed in claim 8, wherein said plurality of arms are biased such that the plurality of arms disengage the insert when the sleeve is not located over the extracting member.

10. An extraction device as claimed in claim 3, wherein said support comprises a hollow cylindrical member and said extracting member comprises a central column extending axially through said support, and wherein a locking means is provided for preventing, in use, the relative rotation of the central column and the support to ensure that all the turning force of the screw means is converted to the axial force.

* * * * *